United States Patent [19]

Berkelhammer et al.

[11] 4,110,345

[45] Aug. 29, 1978

[54] 2,2-DIFLUORO-1,3-BENZODIOXOLE-5-(α-ALKYL)-ACETIC ACIDS, AND THEIR USE FOR THE PREPARATION OF INSECTICIDES AND ACARICIDES

[75] Inventors: Gerald Berkelhammer, Princeton, N.J.; Venkataraman Kameswaran, Levittown, Pa.

[73] Assignee: American Cyanamid Company, Stamford, Conn.

[21] Appl. No.: 774,088

[22] Filed: Mar. 3, 1977

[51] Int. Cl.² ............................................. C07D 317/44
[52] U.S. Cl. ............................... 260/340.5 R; 424/282
[58] Field of Search .................................. 260/340.5 R

[56] References Cited

U.S. PATENT DOCUMENTS 3,378,592    4/1968    Lutz .................................. 260/537 X

FOREIGN PATENT DOCUMENTS 4,742,760   12/1972   Japan ..................................... 260/340.5

*Primary Examiner*—Ethel G. Love
*Attorney, Agent, or Firm*—H. G. Jackson

[57] ABSTRACT

The invention is 2,2-difluoro-1,3-benzodioxole-5-(α-alkyl)acetic acids, the preparation thereof and the use of the acids for the preparation of insecticidal and acaricidal compounds.

9 Claims, No Drawings

2,2-DIFLUORO-1,3-BENZODIOXOLE-5-(α-ALKYL)-ACETIC ACIDS, AND THEIR USE FOR THE PREPARATION OF INSECTICIDES AND ACARICIDES

The prior art is replete with references to various esters of substituted phenylacetic acids as pesticidal agents useful for the control of a variety of insects and mites, for instance Sumitomo Chemical Company Limited discloses in South African Patent Application No. 73/4462 generically a large number of these pheylacetic acid esters. However, none of the art references anticipate, nor is it predictable therefrom that the novel acids of the present invention, when esterified with a suitable alcohol, would yield highly effective insecticidal and acaricidal agents.

Surprisingly we have found that the novel acids of the invention represented by formula:

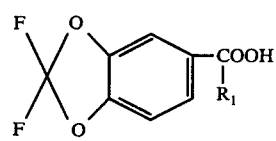

(I)

wherein $R_1$ is lower alkyl and preferably, ethyl, n-propyl or i-propyl and the optical isomers thereof, when esterified with m-phenoxybenzyl alcohol or α-cyano-m-phenoxybenzyl alcohol, yield highly effective insecticidal and acaricidal agents.

Advantageously, 2,2-difluoro-1,3-benzodioxole-5-(α-alkyl)acetic acids of the invention can be prepared by using 5-methyl-1,3-benzodioxole (VII) as a starting material. The process for the preparation involves 6 steps, the first of which is the halogenation of the 5-methyl-1,3-benzodioxole (VII) with a halogenating agent, such as phosphorus pentachloride in the presence of an inert solvent such as toluene to yield the corresponding 2,2-dichloro-5-methyl-1,3-benzodioxole (VI). This compound (VI) is then converted to the corresponding 2,2-difluoro-5-methyl-1,3-benzodioxole (V) with antimony trifluoride in an inert solvent such as dioxane. Next, the thus obtained 2,2-difluoro-5-methyl-1,3-benzodioxole (V) is converted to the corresponding 5-halomethyl derivative by halogenation with bromine, chlorine, N-bromosuccinimide (NBS) and the like. This reaction is preferably conducted in the presence of an inert solvent such as carbon tetrachloride, and a radical initiator such as light, benzoyl peroxide, or azo-bis-isobutyronitrile, to yield 2,2-difluoro-5-halomethyl-1,3-benzodioxole (VI). The formula (IV) compound is then readily converted to the corresponding acetonitrile (III) by reaction with sodium or potassium cyanide in the presence of dimethylsulfoxide (DMSO), ethanol or the like at an elevated temperature. This acetonitrile (III) is readily alkylated when treated with an alkyl halide in the presence of a base and an inert solvent. Crown ethers have been found to be useful catalysts in this reaction. The α-alkylacetonitrile formed in the above reaction is depicted by formula (II), and hydrolysis of this formula (II) α-alkylacetonitrile, using an alkali metal hydroxide in the presence of an alkylene glycol and water, yields the novel formula (I) 2,2-difluoro-1,3-benzodioxole-5-(α-alkyl)acetic acids.

With regard to the compounds of the present invention as depicted by formula (I), it should also be understood that various optical isomers do result from the preparations described, since a chiral center is present at the α-carbon atom and $d$ and $l$ isomeric pairs are formed.

The above reactions are graphically illustrated in Flow Diagram I below.

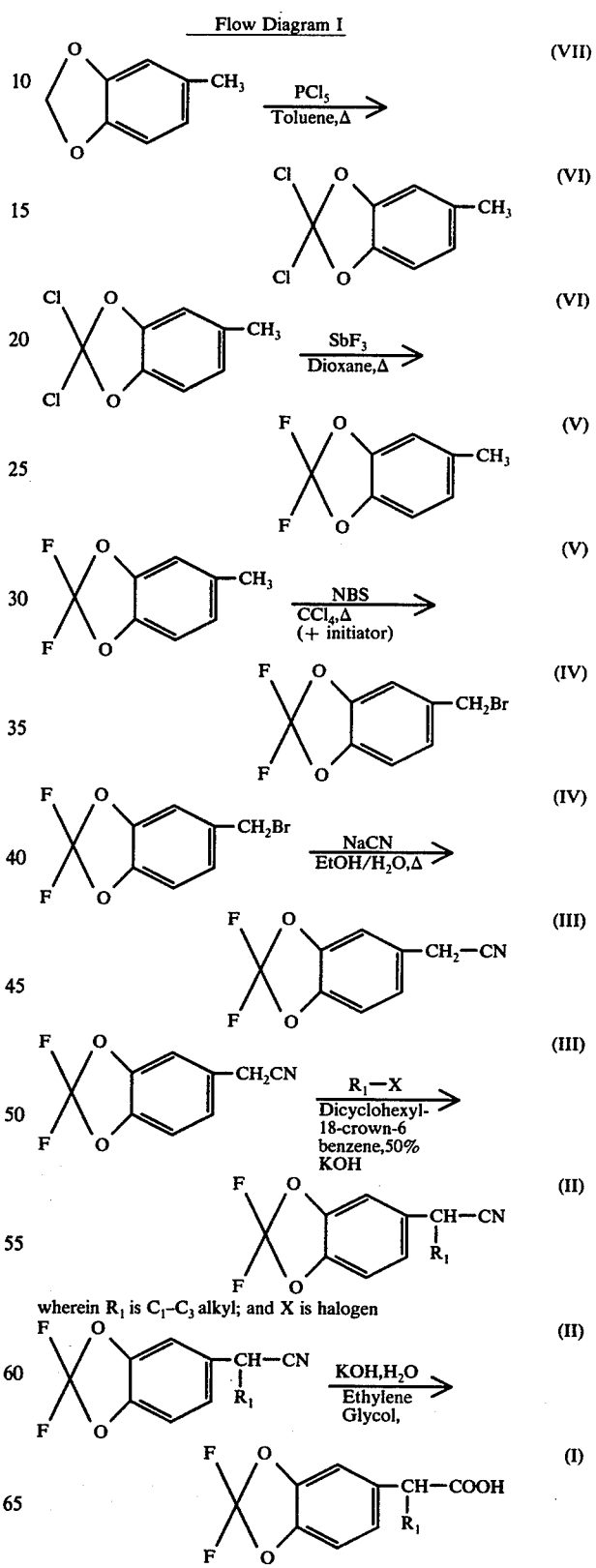

wherein $R_1$ is $C_1$–$C_3$ alkyl; and X is halogen

Advantageously, the insecticidal-acaricidal m-phenoxybenzyl esters of the novel formula (I) 2,2-difluoro-1,3-benzodioxole-5-(α-alkyl)acetic acids can be prepared by reacting a formula (I) acid halide, preferably chloride, with m-phenoxybenzyl alcohol or a substituted m-phenoxybenzyl alcohol. The reaction is generally conducted in the presence of an inert solvent such as diethyl ether, benzene, toluene and the like, at a temperature between about 10° and 30° C in the presence of an acid acceptor. Among the acid acceptors that can be employed are the tertiary organic amines, trimethylamine, triethylamine and pyridine. This reaction can be illustrated as follows:

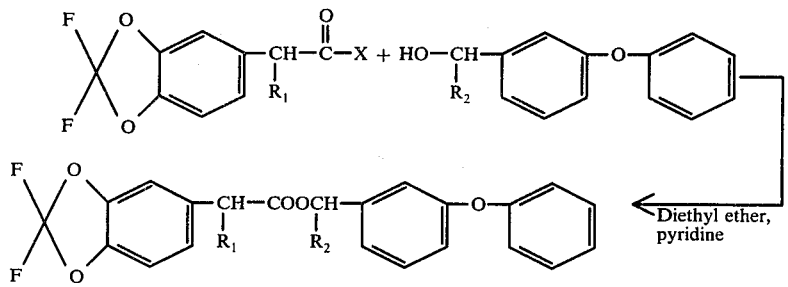

wherein $R_1$ is $C_1$-$C_3$ alkyl; $R_2$ is hydrogen or cyano, and X is halogen, preferably chlorine. The above depicted acid halide is conveniently prepared from the corresponding formula (I) 2,2-difluoro-1,3-benzodioxole-5-(α-alkyl)acetic acid by treating same with thionyl chloride, thionyl bromide or the like, preferably in the presence of an aromatic solvent such as benzene or toluene at elevated temperatures.

The m-phenoxybenzyl esters and α-cyano-m-phenoxybenzyl esters of formula (I) 2,2-difluoro-1,3-benzodioxole-5-(α-alkyl)acetic acids represented by formula (A) below wherein $R_1$ and $R_2$ are as described.

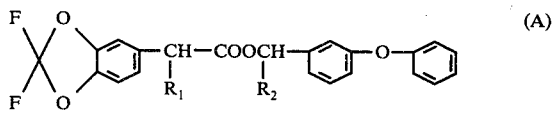

are highly effective as contact and stomach poisons for ixodid ticks and for a variety of insects, particularly Dipterous, Lepidopterous, Coleopterous and Homopterous insects. They are unusual among pyrethroids, in that they exhibit an extended residual insecticidal activity on plant tissue, they are effective in the soil, and are surprisingly effective for the control of ixodidae and the protection of animals against attack by insects and ixodidae when administered to the animals orally or parenterally or applied thereto as a topical insecticidal or acaricidal formulation.

The insecticidal and acaricidal compounds of formula (A) prepared from the novel 2,2-difluoro-1,3-benzodioxole-5-(α-alkyl)acetic acids (I) of the present invention may also be used in combination with other biological chemicals, for example pyrethroid synergists such as piperonyl butoxide, sesamex or n-octyl sulfoxide of isosafrole. Alternatively, they may also be used in combination with conventional insecticides such as the phosphates, carbamates, halobenzoylureas and the like.

To achieve control of insects, including soil insects, which attack growing plants and/or harvested crops, the insecticidal compounds prepared from the above novel acids of formula (I), may be applied to the foliage of plants, the insect's habitat and/or the insect's food supply.

The above insecticides may be formulated as liquid concentrates, emulsifiable concentrates, dusts, granulates, wettable powders and the like, by conventional methods.

For use as animal systemic insecticidal and acaricidal agents, formula (A) compounds may be administered to the animal host either orally or parenterally. For such use, the compounds may be formulated as feed additives, pills, boluses, tablets, oral drenches, implants, injectables and the like, using pharmaceutically acceptable carriers, diluents, solvents and the like.

The invention is further described by the examples set forth below.

EXAMPLE 1

Preparation of 2,2-Dichloro-5-methyl-1,3-benzodioxole

A slurry of 5-methyl-1,3-benzodioxole (52.6 g, 0.387 mole) and phosphorus pentachloride (162.4 g) in toluene is stirred and heated at 70° C for 2 hours. The temperature is then raised to 90° C over 30 minutes and held for 4 hours. Phosphorus trichloride is distilled off at atmospheric pressure. Vacuum distillation yields 73.4 g (92% yield) of title product: 2,2-dichloro-5-methyl-1,3-benzodioxole; $n_D^{24}$ 1.5325; b.p. 78° C to 82° C (at 0.4 mm); nmr (CDCl$_3$) δ 2.28 (S 3H), 6.8 (m 3H).

EXAMPLE 2

Preparation of 2,2-Difluoro-5-methyl-1,3-benzodioxole

Dry dioxane (172 ml) and antimony (III) fluoride are mixed and a part of the solvent is distilled off (57 ml). The mixture is cooled to room temperature and a solution of 2,2-dichloro-5-methyl-1,3-benzodioxole (65.0 g, 0.317 mole) in dioxane (68 ml) is added dropwise over 30 minutes. During the addition the temperature of the reaction mixture rises to 42° C. The solution is refluxed for 7 hours, poured into a mixture of concentrated hydrochloric acid (100 ml) and water (100 ml), and extracted with ether (3×100 ml). The ether extracts are combined, washed with water, dried over sodium sulfate and evaporated. The residual oil is distilled under reduced pressure (obtained by using a water-aspirator) to yield 29.3 g (53% yield) of title product: 2,2-difluoro-5-methyl-1,3-benzodioxole; nmr (CDCl$_3$) δ 2.28 (S, 3H), 6.8–6.8 (m, 3H).

EXAMPLE 3

Preparation of 2,2-Difluoro-5-bromomethyl-1,3-benzodioxole

A mixture of 2,2-difluoro-5-methyl-1,3-benzodioxole (29.0 g, 0.169 mole), N-bromosuccinimide (30.1 g, 0.169 mole), benzoyl peroxide (0.5 g) and carbon tetrachloride (50 ml) is refluxed for 2.5 hours. Carbon tetrachloride (50 ml) is then added to the hot reaction mixture and the solids are filtered off. The filtrate and washings are evaporated to yield 41.0 g of title product, a brown oil; nmr (CCl$_4$) δ 4.38 (S, 2H), 6.8–7.4 (m, 3H). The product is used without further purification in the next step.

EXAMPLE 4

Preparation of
2,2-Difluoro-1,3-benzodioxole-5-acetonitrile

To a solution of 2,2-difluoro-5-bromomethyl-1,3-benzodioxole (41.0 g) in absolute alcohol (160 ml) at 60° to 70° C a hot solution of potassium cyanide (22.1 g, 0.34 mole) in water (30 ml) is added. There is a slight exotherm and within 5 minutes potassium bromide separates out of the reaction mixture. The reaction mixture is refluxed for 1.5 hours, cooled and added to ice-water. The mixture is extracted with ether (3×100 ml), the combined extracts are washed with water (2×50 ml), dried over sodium sulfate and evaporated to afford a dark oil. Vacuum distillation yields 21.2 g of title product; b.p. 64° to 67° C (at 0.03 mm); i.r. (neat) 2255 cm$^{-1}$; nmr (CCl$_4$) δ 3.68 (S, 2H), 7.00 (S, 3H).

EXAMPLE 5

Preparation of
2,2-Difluoro-1,3-benzodioxole-5-(α-isopropyl)acetonitrile

A solution of 50% sodium hydroxide (25 ml) is added to a solution of 2,2-difluoro-1,3-benzodioxole-5-acetonitrile (18.0 g, 0.0913 mole), 2-bromopropane (11.23 g, 0.0913 mole), and dicyclohexyl-18-crown-6* (1.7 g, 5 mole percent) in benzene (10 ml). The reaction temperature rises to 44° to 45° C over 15 minutes. The reaction mixture is then stirred at room temperature for 5 hours. More 2-bromopropane (2.8 g, 25 mole percent excess) is added, and the reaction mixture stirred for 3 days. The organic layer is separated, the aqueous layer is extracted with ether (2×50 ml) and the extracts combined with the organic layer. The combined organic solution is washed with water (2×50 ml), dilute hydrochloric acid (50 ml) and water (2×50 ml) and is dried over sodium sulfate. The dry solution is evaporated to afford an oil. Vacuum distillation of this oil yields 16.35 g (75%) of product; b.p. 67° to 69° C (at 0.03 mm); i.r. (neat) 2250 cm$^{-1}$; nmr (CCl$_4$) δ 1.05 and 1.08 (each d, J=7Hz, 6H), 2.1 (m, 1H), 3.68 (d, J=Hz, 1H), 7.05 (S, 3H).

*The structure of dicyclohexyl-18-crown-6 is:

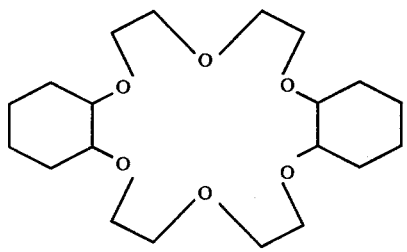

By the above procedure, but substituting 1-iodopropane or iodoethane for 2-bromopropane, 2,2-difluoro-1,3-benzodioxole-5-(α-propyl)acetonitrile and 2,2-difluoro-1,3-benzodioxole-5-(α-ethyl)acetonitrile can be prepared, respectively.

EXAMPLE 6

Preparation of
2,2-Difluoro-1,3-benzodioxole-5-(α-isopropyl)acetic acid

A mixture of 2,2-difluoro-1,3-benzodioxole-5-(α-isopropyl)acetonitrile (13.5 g), potassium hydroxide pellets (20.0 g) in ethylene glycol (100 ml) and water (20 ml) is heated at 140° C with stirring for 14 hours. After cooling, the reaction mixture is poured into water and extracted with ether (2×50 ml). The aqueous portion is cautiously acidified with hydrochloric acid and extracted with ether (3×50 ml). The combined extracts are washed with water (2×50 ml), dried over sodium sulfate and evaporated to dryness. Recrystallization of the solid residue for heptane affords 9.4 g (64%) of product; m.p. 98° to 101° C; i.r. (Nujol mull) 1700 cm$^{-1}$; nmr (CDCl$_3$) δ 0.75 (d, J=8 Hz, 3H), 1.10 (d, J=8Hz, 3H), 2.3 (m, 1H), 3.16 (d, J=10Hz, 1H), 7.0–7.2 (m, 3H).

By the above procedure, but substituting 2,2-difluoro-1,3-benzodioxole-5-(α-propyl)acetonitrile or 2,2-difluoro-1,3-benzodioxole-5-(α-ethyl)acetonitrile for 2,2-difluoro-1,3-benzodioxole-5-(α-isopropyl)acetonitrile, 2,2-difluoro-1,3-benzodioxole-5-(α-propyl)acetic acid and 2,2-difluoro-1,3-benzodioxole-5-(α-ethyl)acetic acid can be prepared, respectively.

EXAMPLE 7

Preparation of
2,2-Difluoro-1,3-benzodioxole-5-(α-isopropyl)-acetyl chloride

A solution of 2,2-difluoro-1,3-benzodioxole-5-(α-isopropyl)acetic acid (5.16 g, 0.02 mole) and thionyl chloride (2.0 ml) in benzene (10 ml) is refluxed for 4 hours. Evaporation of the solvent and excess thionyl chloride affords the product, which can be used without further purification in the subsequent steps.

By the above procedure, using the appropriate 2,2-difluoro-1,3-benzodioxole-5-(α-alkyl)acetic acids, 2,2-difluoro-1,3-benzodioxole-5-(α-propyl)acetyl chloride and 2,2-difluoro-1,3-benzodioxole-5-(α-ethyl)acetyl chloride can be prepared, respectively.

EXAMPLE 8

Preparation of α-Cyano-m-phenoxybenzyl ester of
2,2-difluoro-1,3-benzodioxole-5-(α-isopropyl)acetic acid A solution of 2,2-difluoro-1,3-benzodioxole-5-(α-isopropyl)acetyl chloride (0.01 mole) in ether (10 ml) is added to a solution of α-cyano-m-phenoxybenzyl alcohol (2.03 g, 90 mole percent) and pyridine (0.8 g) in ether (25 ml) at room temperature. The reaction mixture is stirred overnight at room temperature. The solids are filtered off and washed with ether. The filtrate and washings are combined and evaporated to yield an oil. The oil is purified by dry column chromatography on silica gel using 1:1 methylene chloride-hexane as eluent to afford 3.40 g (73%) of product; nmr (CDCl$_3$) 0.6–1.1 (set of d, 6H), 2.3 (m, 1H), 3.2 (d, J=10Hz, 1H), 6.30 and 6.35 (S, 1H), 6.8–7.5 (m, 12H).

The α-propyl and α-ethyl analogs are made in similar fashion starting with the corresponding α-propyl and α-ethylacetyl chlorides of Example 7.

EXAMPLE 9

Residual insecticidal activity obtained with foliar treatment of cotton plants Young cotton plants with at least two expanded true leaves growing in 10 cm plastic pots were dipped, usually one leaf at a time in a 65% acetone-35% water solution of test compound with agitation for three seconds. The concentration of the compound in the solutions was 30 ppm, 100 ppm, 300 ppm or 900 ppm of active ingredient.

After the leaves had dried, two leaves from each of two plants were excised and placed in petri dishes (90 mm × 100 mm) on moist filter paper (9 cm Whatman No. 1). Five third-instar tobacco budworm larvae were placed on each leaf and the petri dish capped. The infested dishes were than placed in a holding room with continuous light, ambient temperature of 80° F and 50% r.h. Larval counts were made after 72 hours.

The remaining plants were placed under high intensity lights in the greenhouse adjusted to provide 14 hours of light per day. Leaf samples were assayed with third instar tobacco budworm larvae after 3, 7, 10 and 14 days exposure in the greenhouse.

The data obtained are summarized in Table I.

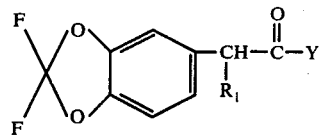

wherein $R_1$ is lower alkyl and Y is hydroxyl or halogen, and the optical isomers thereof.

2. A compound according to claim 1, wherein $R_1$ is ethyl, n-propyl or i-propyl.

3. A compound according to claim 1, 2,2-difluoro-1,3-benzodioxole-5-(α-ethyl)acetic acid.

4. A compound according to claim 1, 2,2-difluoro-1,3-benzodioxole-5-(α-propyl)acetic acid.

5. A compound according to claim 1, 2,2-difluoro-1,3-benzodioxole-5-(α-isopropyl)acetic acid.

6. A method for the preparation of a compound having the formula (I)

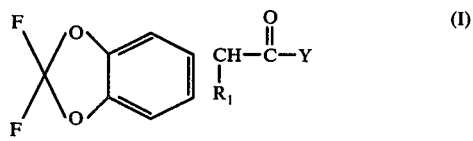

Table I

Residual Insecticidal Activity of a Test Compound on Cotton Plants Using Third-Instar Tobacco Budworm Larvae for Bioassay

| Compound | Rate ppm | 0* | 3 | 7 | 10 | 14 |
|---|---|---|---|---|---|---|
| F-benzodioxole-CH(CH(CH₃)₂)-COOCH(CN)-C₆H₄-O-C₆H₅ | 30 | 45 | 0 | 10 | 10 | 10 |
| | 100 | 90 | 55 | 55 | 65 | 10 |
| | 300 | 95 | 90 | 100 | 90 | 95 |
| | 900 | 100 | 100 | 100 | 100 | 100 |
| Control | — | 0 | 0 | 5 | 0 | 13 |

\* = Average % Mortality 20 TBW/Point

EXAMPLE 10

The effectiveness of an acaricide prepared from the novel 2,2-difluoro-1,3-dioxole-5-(α-alkyl)acetic acids of the present invention for the control of adult *Boophilus microplus* ticks is determined in the following test wherein the test compound is dissolved in 10% acetone-90% water mixture in sufficient amounts to give solutions containing 125, 52.6, 31.2, 15.6 or 7.3 ppm of test compound.

Adult engorged female ticks are dipped in the test solutions for 3 seconds and placed in individual containers and held for 48 hours in a room maintained at 80° F and 50% r.h. At the end of the holding period the ticks are examined and egg deposits counted. Engorged females that do not deposit eggs are considered dead. Data obtained are reported below in Table II.

wherein $R_1$ is lower alkyl, Y is hydroxy, chlorine or bromine, and the optical isomers thereof, comprising reacting a compound of formula (II)

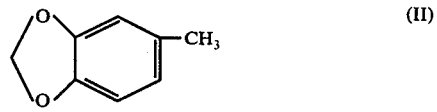

with a chlorinating agent in the presence of an inert solvent to obtain a compound of formula (III)

Table II

| Compound | Percent Adult Tick Mortality at Concentration (ppm) | | | | |
|---|---|---|---|---|---|
| | 125 | 62.5 | 31.2 | 15.6 | 7.3 |
| F-benzodioxole-CH(CH(CH₃)₂)-COOCH(CN)-C₆H₄-O-C₆H₅ | 98.3 | 99.7 | 88.4 | 85.8 | 80.2 |

We claim:

1. A compound having the formula:

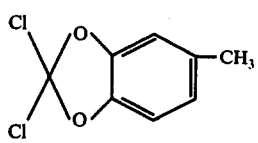
(III)

reacting the compound of formula (III) with antimony trifluoride in the presence of an inert solvent to obtain a compound of formula (IV)

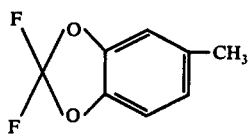
(IV)

reacting the formula (IV) compound with bromine, chlorine or N-bromosuccinimide in the presence of an inert solvent and a free radical initiator to obtain a compound of formula (V)

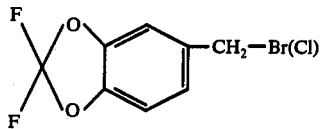
(V)

converting the above formula (V) compound with an alkali metal cyanide to the corresponding acetonitrile of formula (VI)

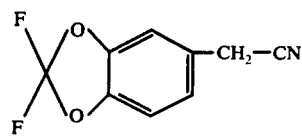
(VI)

alkylating the above nitrile with a lower alkyl halide in the presence of a base and an inert solvent to a compound of formula (VII)

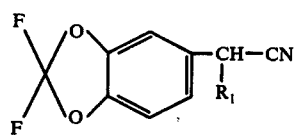
(VII)

wherein $R_1$ is lower alkyl, hydrolyzing formula (VII) compound with an alkali metal hydroxide in the presence of water and a glycol at an elevated temperature to obtain the formula I compound wherein Y is hydroxyl or reacting the formula I product of the reaction with thionyl chloride or thionyl bromide in the presence of an inert solvent to produce a formula I compound wherein Y is chlorine or bromine.

7. A method according to claim 6, wherein $R_1$ is ethyl, propyl or isopropyl.

8. A method according to claim 7, wherein the product is the compound 2,2-difluoro-1,3-benzodioxole-5-(α-isopropyl)-acetic acid.

9. A method according to claim 7 wherein the product is the compound 2,2-difluoro-1,3-benzodioxole-5-(α-isopropyl)-acetyl chloride.

* * * * *